US007123358B2

(12) United States Patent
Tuschel et al.

(10) Patent No.: US 7,123,358 B2
(45) Date of Patent: Oct. 17, 2006

(54) METHOD FOR RAMAN IMAGING OF SEMICONDUCTOR MATERIALS

(75) Inventors: David Tuschel, Monroeville, PA (US); Patrick J. Treado, Pittsburgh, PA (US); Joseph E. Demuth, Pittsburgh, PA (US)

(73) Assignee: ChemImage Corporation, Pittsburgh, PA (US)

(*) Notice: Subject to any disclaimer, the term of this patent is extended or adjusted under 35 U.S.C. 154(b) by 353 days.

(21) Appl. No.: 10/610,481

(22) Filed: Jun. 30, 2003

(65) Prior Publication Data

US 2004/0004715 A1    Jan. 8, 2004

Related U.S. Application Data

(63) Continuation-in-part of application No. 09/976,391, filed on Oct. 12, 2001, now Pat. No. 6,734,962, and a continuation-in-part of application No. 09/800,953, filed on Mar. 7, 2001, now Pat. No. 6,717,668, and a continuation-in-part of application No. 09/619,371, filed on Jul. 19, 2000, now Pat. No. 6,788,860.

(60) Provisional application No. 60/422,604, filed on Oct. 31, 2002, provisional application No. 60/239,969, filed on Oct. 13, 2000, provisional application No. 60/187,560, filed on Mar. 7, 2000, provisional application No. 60/144,518, filed on Jul. 19, 1999.

(51) Int. Cl.
*G01J 3/44* (2006.01)
*G01N 21/00* (2006.01)

(52) U.S. Cl. .................. 356/301; 356/302; 356/237.4; 356/237.5

(58) Field of Classification Search .................. 356/73, 356/301, 237.2–237.5, 302
See application file for complete search history.

(56) References Cited

U.S. PATENT DOCUMENTS

| 5,048,959 | A | * | 9/1991 | Morris et al. | ............... 356/301 |
| 6,069,690 | A | * | 5/2000 | Xu et al. | ....................... 356/73 |
| 6,151,119 | A | * | 11/2000 | Campion et al. | ........... 356/630 |
| 6,473,174 | B1 | * | 10/2002 | Ballast et al. | ............... 356/301 |
| 6,545,755 | B1 | * | 4/2003 | Ishihama et al. | ........... 356/301 |
| 6,870,612 | B1 | * | 3/2005 | Jiang | .......................... 356/301 |

OTHER PUBLICATIONS

K. Mizoguchi et al, Micro-Raman characterization of chrystallinity of laser-recrystallized silicon films on SiO2 insulators, Journal of Applied Physics, May 1999, vol. 85, No. 9, pp. 6758-6752.*

Mizoguchi et al. "Raman image study of flash-lamp annealing of ion-implanted silicon" *Journal of Applied Physics* 77 (7) Apr. 1, 1995, pp. 3388-3392.

Othonos et al., "Raman spectroscopy and spreading resistance analysis of phosphorous implanted and annealed silicon", *Journal of Applied Physics* 75 (12) Jun. 15, 1994, pp. 8032-8038.

Othonos et al., "Multi-wavelength Raman probing of phosphorus implanted silicon wafers", *Nucl. Instr. and Meth. in Phys. Rev. B.* 117 (1996) pp. 367-374.

(Continued)

*Primary Examiner*—Layla G. Lauchman
(74) *Attorney, Agent, or Firm*—Morgan, Lewis & Bockius LLP

(57) ABSTRACT

An ion implanted semiconductor surface is illuminated with a flood illumination of monochromatic radiation, and an image of the surface is taken using light which has been Raman scattered. The illumination and imaging system are calibrated by flood illuminating a uniformly Raman scattering surface.

11 Claims, 9 Drawing Sheets

Raman Image of Ion Implanted Si

Raman Scattered Light at 520 cm⁻¹

Implant: 2.7 x 10¹² P cm⁻²

Reflected White Light

15 μm

OTHER PUBLICATIONS

Christofides et al., "Reconstruction mechanisms in ion implanted and annealed silicon wafers",*Defect and Diffusion Forum* vols. 117-118 (1985), pp. 45-64.

Ishioka et al. "Reduction in Raman Intensity of Si (1 1 1) Due to Defect Formation During Ion Irradiation", *Solid State Communications*, vol. 96, No. 6, pp. 387-390(1995).

Dey et al, "Raman scattering characterization of Si(100) implanted with mega-electron-volt Sb",*Journal of Applied Physics* 87 (3) Feb. 1, 2000, pp. 1110-1116.

Jain et al, "Raman scattering from ion-implanted silicon" *Physical Review B*. vol. 32, No. 10, Nov. 15, 1985, pp. 6688-6691.

Dewilton et al, "Raman Spectroscopy for Nondestructive Depth Profile Studies of Ion Implantation in Silicon",*J. Electrochem. Soc.*: Solid State Science and Technology, ,May 1986, pp. 988-993.

Zhang et al "Details of the Damage Profile in Self-Ion-Implanted Silicon", vol. 45 *Journal of Raman Spectrocsopy*, pp. 515-520 (1994).

Gorelick, "Raman And Non-Linear Light Scattering From Undersurface Layers Of Ion Implanted Silicon Crystals", *materials Science Forum*, vol. 173-174 (1995) pp. 237-242.

Nakashima et al. "Raman microprobe study of recrystallization in ion-implanted and laser-annealed polycrystalline silicon" *Journal of Applied Physics* 54 (5) May. 1983, pp. 2611-2617.

Shukla et al, "Raman scattering from ultraheavily-ion-implanted and laser-annealed silicon" *Physical Review B*. vol. 34, No. 12, Dec. 15, 1986, pp. 8950-8953.

Dewilton et al, "A Raman study of the dopant distribution in submicron pn junctions in $B^+$or $BF_2^+$ion implanted silicon", *SPIE vol. 623 Advanced Processing and Characterization of Semiconductors III* 1986, pp. 26-34.

Kirilov et al; "Amorphous phase transformation during rapid thermal annealing of ion-implanted Si", *Mat'l. Res. Soc. Symp. Proc.*, vol. 52 (1986), pp. 131-138.

M.D. Schaeberle and P.J. Treado, "LCTF Raman Chemical Imaging of Semiconductors," Proc. Xvth ICORS, S.A. Asher, Ed (Wiley, Chichester, 1996) 1188-1189.

Patrick J. Treado, Joint Venture Advanced Technology Program (ATP) Proposal, Apr. 7, 1998.

* cited by examiner

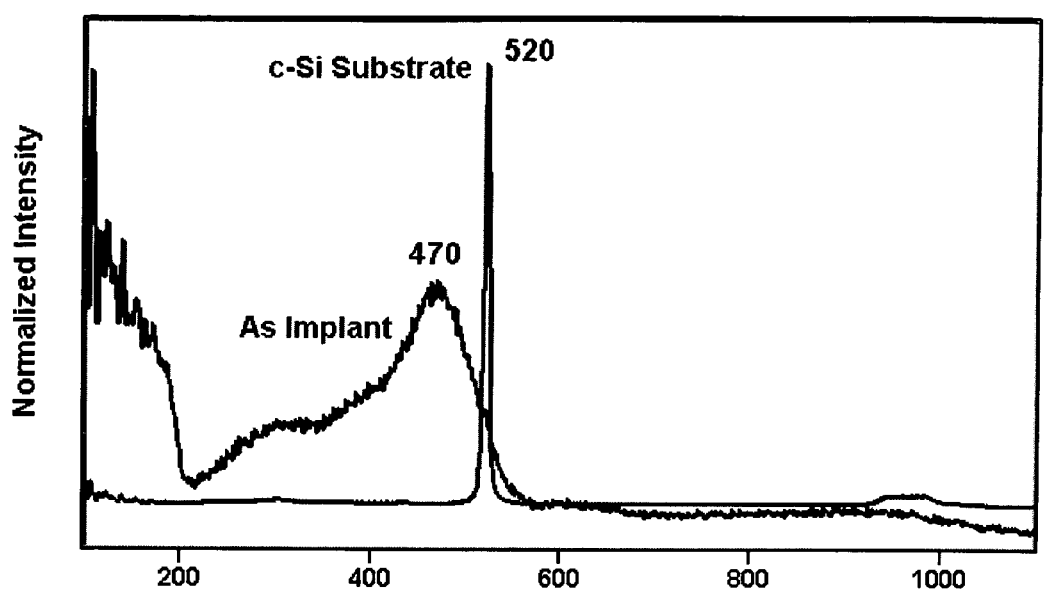
Fig. 1 shows Raman spectra from two different regions. The relative intensity scales have been normalized to the same value for the highest peak in each spectra.

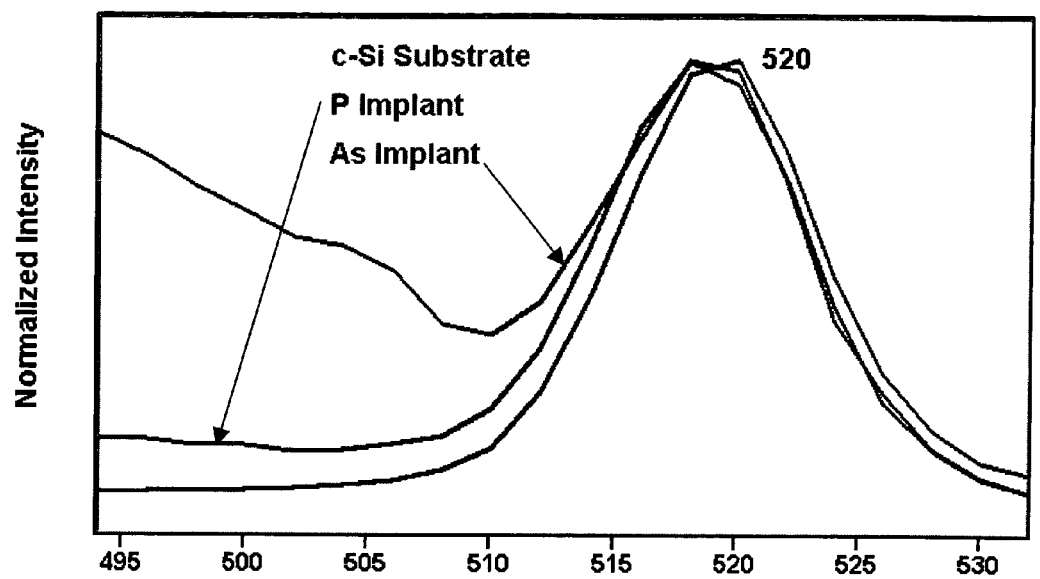
Fig. 2 shows Raman spectra from 490 to 530 cm$^{-1}$ which are all normalized to the peak at 520 cm$^{-1}$.

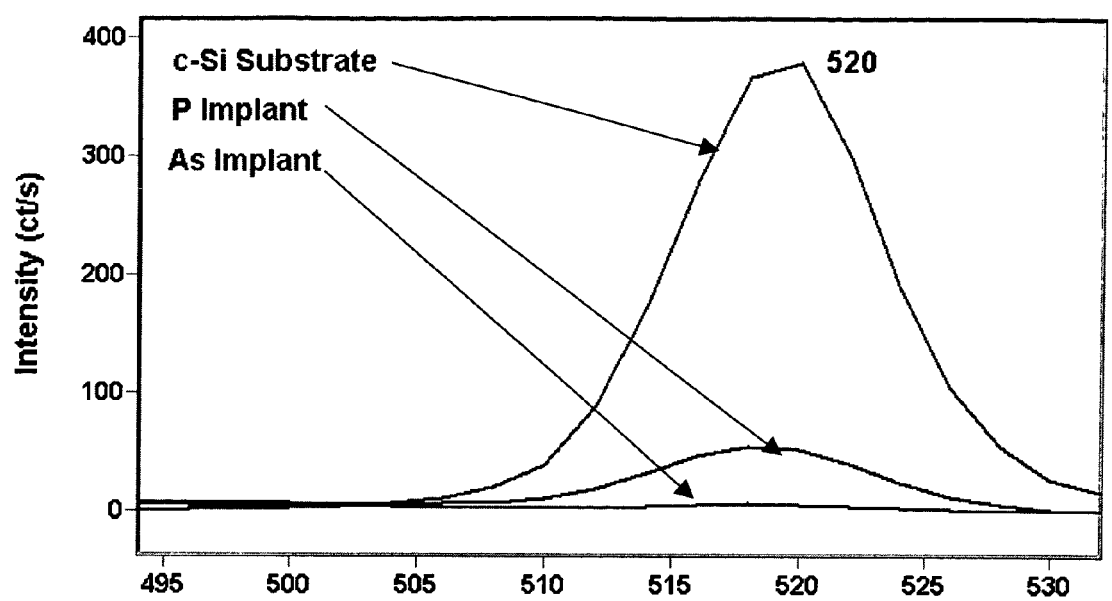
Fig. 3 shows Raman spectra of Fig. 2 plotted on the same scale.

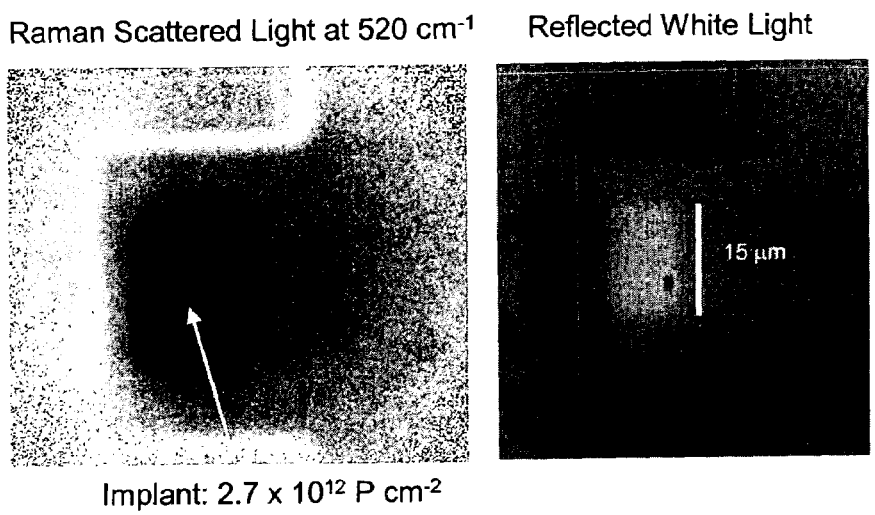
Fig. 4 shows images of a portion of a silicon wafer with a 15 um high rectangular feature which has been implanted with $2.7 \times 10^{12}$ cm$^{-2}$ phosphorus. The Raman image on the left uses the intensity of the 520 cm$^{-1}$ Raman feature where white corresponds to the highest crystalline peak intensity and black to the absence of crystalline silicon.

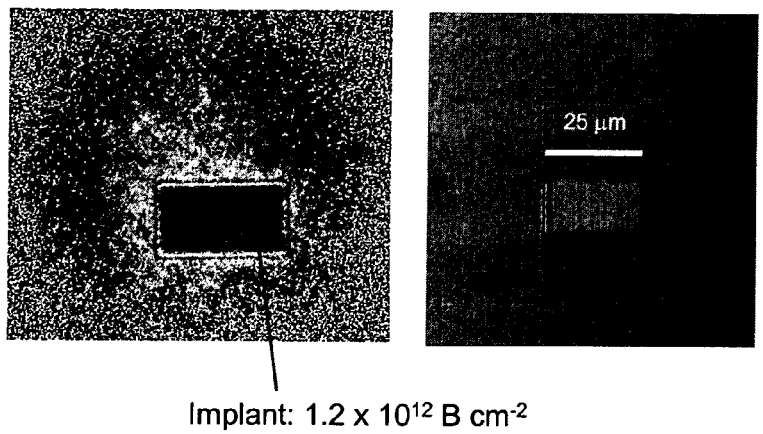
Fig. 5 shows images of a portion of a silicon wafer where the rectangular region 25 um wide is implanted with $1.2 \times 10^{12}$ cm$^{-2}$ boron.

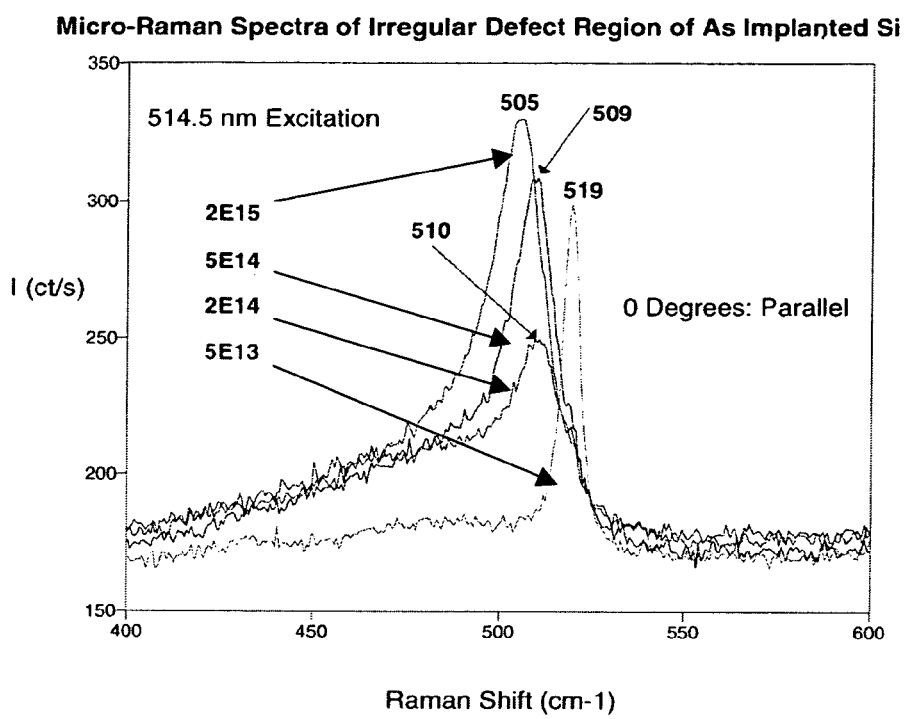
Fig. 6 shows Raman spectra of inclusions in silicon implanted with arsenic ions.

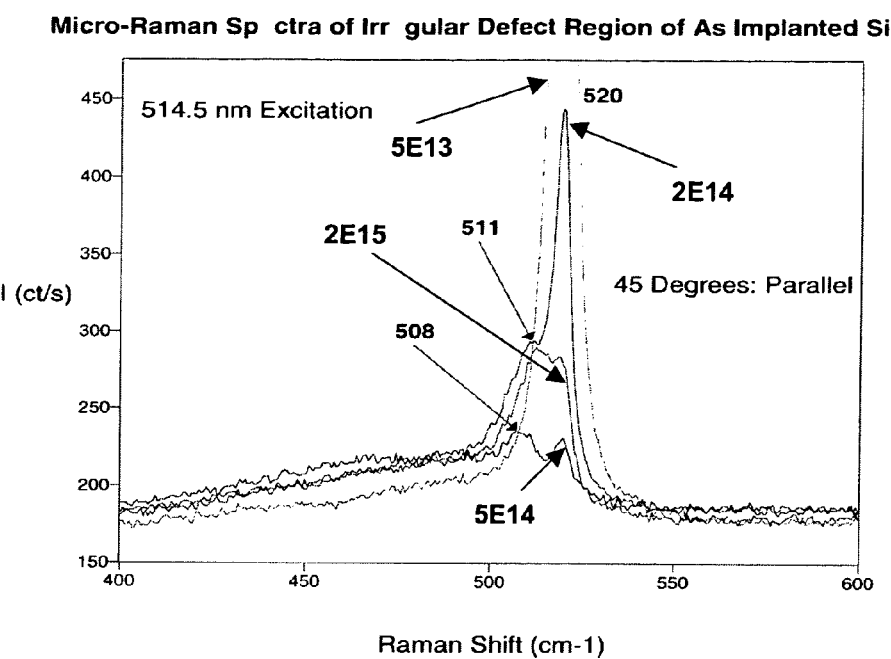
Fig. 7 shows Raman spectra of inclusions in silicon implanted with arsenic ions.

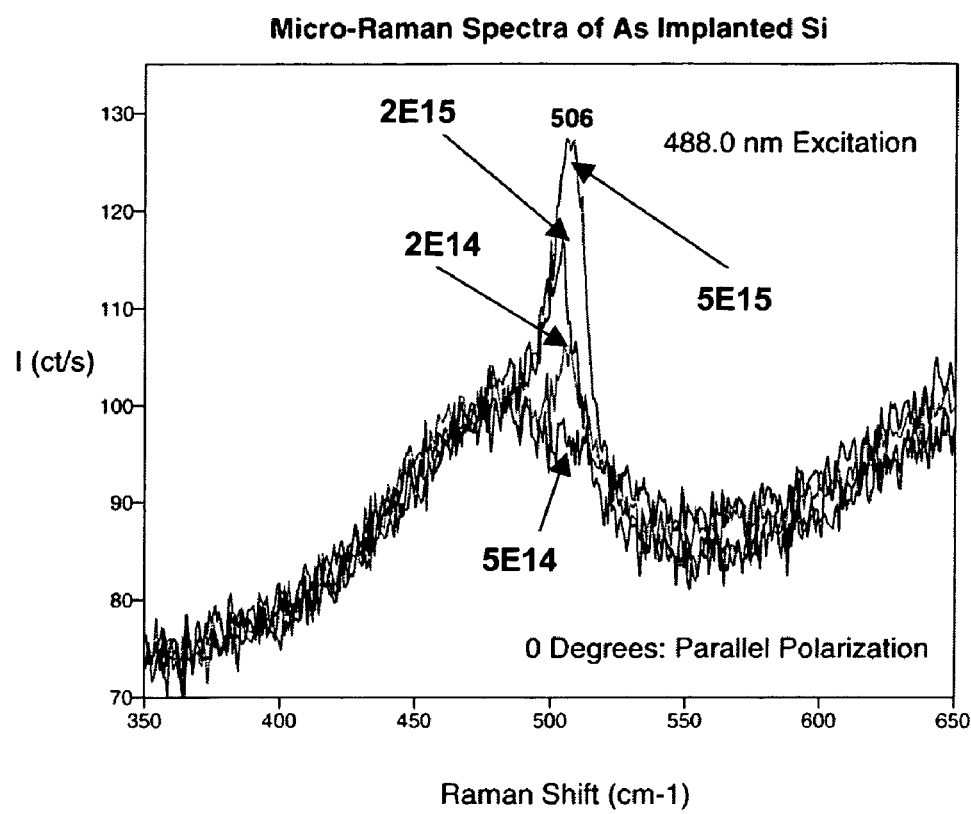
Fig. 8 shows Raman spectra of inclusions in silicon implanted with arsenic ions.

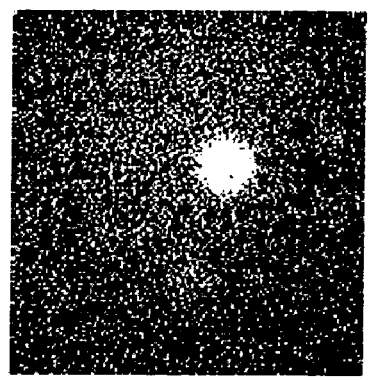
Fig. 9 shows a Raman image of a hexagonal phase inclusion in silicon.

METHOD FOR RAMAN IMAGING OF SEMICONDUCTOR MATERIALS

CROSS REFERENCE TO RELATED APPLICATIONS

This application is a continuation-in-part (CIP): of U.S. Non-Provisional application Ser. No. 09/619,371 filed Jul. 19, 2000 now U.S. Pat. No. 6,788,860 which claims benefit pursuant to 35 U.S.C. § 119(e) of U.S. Provisional Application 60/144,518 filed Jul. 19, 1999; of U.S. Non-Provisional application Ser. No. 09/976,391 filed Oct. 12, 2001 now U.S. Pat. No. 6,734,962 which claims benefit pursuant to 35 U.S.C. § 119(e) of U.S. Provisional Application 60/239,969 filed Oct. 13, 2000; and of U.S. Non-Provisional application Ser. No. 09/800,953 filed Mar. 7, 2001 now U.S. Pat. No. 6,717,668 which claims benefit pursuant to 35 U.S.C. § 119(e) of U.S. Provisional Application 60/187,560 filed Mar. 7, 2000. This application also claims benefit pursuant to 35 U.S.C. § 119(e) of U.S. Provisional Application 60/422,604 filed Oct. 31, 2002. All of the above applications are incorporated herein by reference in their entirety including incorporated material.

FIELD OF THE INVENTION

The invention relates to spectroscopic imaging systems in general and Raman chemical imaging systems in particular. The invention also relates to the use of chemical imaging systems in characterizing ion implanted semiconductors and in particular silicon materials.

BACKGROUND OF THE INVENTION

Chemical imaging is a new scientific discipline, which combines the chemical analysis power of optical spectroscopy, including Raman, infrared, photoluminescence and fluorescence techniques, with high-resolution optical imaging. It has powerful capability for materials characterization, process monitoring, quality control and disease-state determination. This invention relates to a system for obtaining spectroscopically resolved images of materials using electronically tunable imaging spectrometers employing liquid crystal elements.

Raman and infrared image contrast is derived from a material's intrinsic vibrational spectroscopic signature, which is highly sensitive to the composition and structure of the material and its local chemical environment. As a result, Raman and infrared imaging can be performed with little or no sample preparation and are widely applicable for materials research, failure analysis, process monitoring and clinical diagnostics.

Several approaches to Raman imaging have been demonstrated that employ means to simultaneously record spatial and Raman spectral information. Specifically, such Raman imaging data consists of 2 spatial (x,y) locations and one spectral dimension—the Raman intensity as a function of Raman frequency. Almost exclusively, modem Raman imaging methods employ multi-channel charge-coupled device (CCD) detection. CCDs are employed to record two dimensions of the three-dimensional information inherent in Raman image data sets. Raman imaging systems can be differentiated by the means they employ to collect the third dimension of information. Raman imaging systems employing dispersive monochromators coupled to CCDs have been devised that rely on two-dimensional point scanning, one-dimensional line scanning, and spatial multiplexing. In addition, Michelson interferometers have been employed in point scanning systems, while a number of tunable filter spectrometers have been described in the past several years.

Of the imaging spectrometers that have been employed for Raman imaging, including liquid crystal tunable filters (LCTFs), acousto-optic tunable filters (AOTFs) and Fabry-Perot filters, LCTFs are the most effective. In general, tunable filter methods employ wide-field laser illumination in combination with multichannel detection. The two spatial dimensions of the image are recorded directly by the CCD camera, while the multispectral information is acquired by capturing images at discrete wavelengths selected by the tunable filter. Under computer control it is possible to collect a data set with a Raman spectrum at each pixel of the image. An advantage of tunable filters is that they provide image fidelity that is limited only by the number of pixels in the camera. As a result, the use of high-definition detectors allows the efficient collection of high-definition images. Prior to the introduction of LCTFs, a key limitation of tunable filters that had handicapped Raman microscopy had been the lack of the availability of tunable filters that simultaneously provided narrow spectral bandpass, broad free spectral range and high image quality. For example, AOTF Raman imaging systems provide high throughput and broad spectral coverage, but AOTFs have distinct limitations. AOTFs suffer from broad spectral bandpass, and imaging performance is degraded appreciably from the diffraction-limited conditions. In effect, AOTFs provide spectral resolution that is an order of magnitude worse than that of a typical Raman spectrometer, and spatial resolution that is approximately 2.5 times worse than the diffraction limit.

A better alternative to the AOTF is the LCTF. In general, LCTFs are electro-optically controllable spectral bandpass filters that can function from the visible to the near-infrared. A number of LCTF designs have been demonstrated for use in multispectral imaging. LCTFs based on the Lyot filter design have been used primarily as red-green-blue (RGB) color filters and fluorescence imaging filters. A nematic LCTF based on the design of the Lyot birefringent filter has been used in a Raman imaging system. The multistage Lyot filter is comprised of a fixed retardance birefringent element and a nematic liquid crystal wave plate placed between parallel linear polarizers. The nematic liquid crystal wave plates incorporated within the Lyot filter act as electronically controlled phase retarders. The LC wave plates can be adjusted over a continuous range of retardance levels, enabling continuous tunability of wavelength. In general, Lyot filters suffer from low peak transmittance. The two main sources of optical loss in the Lyot LCTFs are absorption in the polarizers and imperfect waveplate action arising from the use of simple $\lambda/2$ plates to construct the wide-field retarder stages. An LCTF based on a Fabry-Perot design has been demonstrated for Raman microscopy. However, Fabry-Perot filters suffer from low transmittance, low out of band rejection efficiency, limited free spectral range and low spectral bandpass (25 $cm^{-1}$). In addition, Fabry-Perot filters are susceptible to thermal-induced drift in spectral bandpass unless contained in temperature-controlled housings.

Raman spectroscopy has been used extensively in the prior art to characterize semiconductor materials such as the elemental semiconductors silicon and germanium, as well as compound semiconductors exemplified by III-V and II-VI semiconductors such as GaAs, GaInAs, GaInAlAs, GaAlInP, GaN, GaP, ZnSe, and CdTe. Early work on these materials used a focused or an unfocused laser beam illuminating a uniform material. Later work used a laser microprobe focused through a high quality micoscope to investigate microscopic features of interest in the materials. Images were obtained by scanning the microscopic laser spot over the surface, and recording the Raman scattered light gathered as a function of time, or by focusing the laser to a line focus and using a two dimensional detector to record one spatial dimension and one wavelength dimension. The material could then be moved in a second spatial dimension to record another scan and so on to build up a three dimensional (two spatial dimensions and one wavelength dimension) image.

OBJECTS OF THE INVENTION

It is an object of the invention to produce an apparatus, a method, and a system for rapidly characterizing semiconductor materials with high spatial and spectroscopic resolution.

It is an object of the invention to produce an apparatus, a method, and a system for rapidly characterizing ion implanted semiconductor material with high spatial and spectroscopic resolution.

It is an object of the invention to produce a sensitive apparatus, a method, and a system for characterizing ion implanted semiconductor material with high spatial and spectroscopic resolution, wherein the ion implantations changes the optical and electronic properties of the material only slightly from those of single crystal semiconductor.

SUMMARY OF THE INVENTION

An ion implanted semiconductor material is illuminated by a flood illumination of narrow bandwidth electromagnetic radiation. Raman shifted light from the material is imaged in two spatial dimensions to characterize the material. In particular, a first region of single crystal semiconductor is imaged in the same image at the same time as a second region of perturbed semiconductor material, and a comparison of the spectrum from the first and second regions is used to characterize the perturbed semiconductor material.

BRIEF DESCRIPTION OF THE DRAWINGS

FIG. 1 shows Raman spectra of two different regions.

FIG. 2 shows Raman spectra from 490 to 530 $cm^{-1}$.

FIG. 3 shows Raman spectra of FIG. 2 plotted on the same scale.

FIG. 4 shows an image of a portion of a silicon wafer with regions implanted with $2.7 \times 10^{12}$ $cm^{-2}$ phosphorus.

FIG. 5 shows an image of a portion of a silicon wafer with a region implanted with $1.2 \times 10^{12}$ $cm^{-2}$ boron.

FIG. 6 shows Raman spectra of inclusions in silicon implanted with arsenic ions.

FIG. 7 shows Raman spectra of inclusions in silicon implanted with arsenic ions.

FIG. 8 shows Raman spectra of inclusions in silicon implanted with arsenic ions.

FIG. 9 shows a Raman image of a hexagonal phase inclusion in silicon.

DETAILED DESCRIPTION OF THE INVENTION

The inventors have realized that prior art imaging techniques were deficient in that the incident light was not reproducible enough over time to produces high enough quality images for materials characterization. In particular, inventors have realized that the prior art has no mechanism to record a comparison Raman signal simultaneously in the same image with the Raman signal from regions of interest. The present invention solves this previously unrecognized problem.

John Evans described a 'split-element' design that addresses the inefficiency of the Lyot design filters. The 'split-element' design cuts the number of polarizers in half, plus one, reducing the absorbance of light due to the polarizers. In addition, the $\lambda/2$ waveplates are eliminated providing enhanced optical throughput. This yields an improved filter transmission ranging from 1.55–3.1 times that of the Lyot filter.

Imaging spectrometers include Fabry Perot angle rotated or cavity tuned liquid crystal (LC) dielectric filters, acousto-optic tunable filters, and other LC tunable filters (LCTF) such as Lyot Filters and variants of Lyot filters such as Solc filters and the most preferred filter, an Evan's split element liquid crystal tunable filter, which is described in the March (1999) issue of Analytical Chemistry on page 175A. Other preferred wavelength filtering means comprise polarization-independent imaging interferometers such as Michelson, Sagnac, Twynam-Green, and Mach-Zehnder interferometers.

Unlike other tunable elements for Raman imaging, the LCTF is free of optical distortions, spectral leakage, or image shift with tuning. The first generation (Lyot) LCTFs were designed to operate with green laser excitation and operated only to 650 nm. Evans Split-Element LCTFs operate from 420–720 nm and from 650–1100 nm, as determined by the choice of polarizers. Operation in the red wavelength region has advantages, particularly for the analysis of biological systems. For example, operation in the red wavelength region provides enhanced fluorescence rejection when combined with efficient diode laser sources and takes full advantage of the enhanced red sensitivity of recent generation CCD detectors.

Compared to existing, non-imaging systems, the Raman LCTF system adds the powerful ability to visualize the distribution (morphology and architecture) of chemical and crystal species in heterogeneous samples with molecular compositional specificity. Raman images can be collected rapidly, non-invasively, with limited or no sample preparation, at high spatial resolution (<250 nm) and with high fidelity where the spatial fidelity is limited by the number of pixels on the CCD detector. Most importantly, every image pixel has associated with it a Raman spectrum whose quality is comparable to that obtained with conventional non-imaging spectrometers.

Raman is so broadly applicable because most materials exhibit characteristic 'fingerprint' Raman vibrational spectra. Generally accepted practice in performing Raman microscopy is to use non-imaging techniques such as a scanned laser Raman microspot, which yield spectral data but limited (or inefficient) collection of spatial data. Samples exhibiting complex morphologies and well characterized spectral bands are best studied using LCTF technology because of the inherent efficiency of analyzing all spatial channels simultaneously in a massively parallel fashion. The LCTF Raman chemical imaging measurement identifies the presence and/or location of an analyte species in a sample by imaging at the characteristic analyte Raman spectral bands. In general, it is not necessary to have a complete Raman spectrum at each image pixel in order to obtain meaningful and chemically relevant image contrast. This is especially due in part to the redundancy of a typical Raman spectrum.

Often only several regions of the spectrum are needed to generate analyte-specific image contrast. The Evans Split-Element LCTF represents a significant technology for Raman imaging because it provides spectral resolution comparable to a single stage dispersive monochromator while also providing diffraction-limited spatial resolution. This performance is provided without moving mechanical parts in a computer controlled device which allows automated operation.

The LCTF is introduced into the optical path of an infinity corrected optical microscope. The light rays from the object are collected by the microscope objective and turned into substantially parallel rays, which then pass through the LCTF and continue to the detector apparatus. The object is illuminated, generally through the objective, so that the field of view of the microscope, or a substantial part of the field of view, is illuminated substantially uniformly. A typical imaging array may have from $10^4$ or $10^5$ to $10^7$ pixels. Resolution down to 250 nm in such microscopes are available. Thus, a field of view may have an area A of 6.25, 62.5 or 6,250 square micrometers. For quantitative work, it is important to illuminate the field of view with a flood illumination. Flood illumination is defined in this specification as illumination which illuminates substantially all of the field of view with substantially uniform illumination. The illumination may be part of a "top hat" profile or part of Gaussian beam which extends beyond the field of view, but there must be sufficient illumination at the edge of the field of view that quantitative comparison of Raman intensity can be made of features in one part of the field of view with features in another part of the field of view. Any patterns in the substantially uniform illumination must remain substantially the same as the field of view is changed, so that from image to image the same illumination intensity pattern may be assumed.

The inventors have found that a measure of the illuminating intensity, such as imaging the incident, reflected or scattered illumination wavelength, is not sufficient to calibrate the Raman scattering intensity. For calibration purposes, the inventors have found that a Raman image of a uniformly Raman scattering field of view, for example a uniform crystal silicon area, is preferable. The inventors generally anticipate that the reflected light from the illuminating beam is not Lambertian, and retains much of the angular information contained in the illumination beam. The Raman scattered light, however, is generated under the surface of the specimen, and a Raman generated photon will in general have a different direction than the illumination photon which generated it. If the Raman scattering is isotropic, the Raman light exiting the specimen will be have a Lambertian spatial distribution. For an optical imaging system with a large numerical aperture, there is a vignetting effect, and a higher percentage of the Raman photons emitted from the center of the field of view will be captured than those emitted from the edges of the field of view. Even if a field of view is illuminated absolutely uniformly, the number of Raman scattered photons per unit area captured in the image is less towards the edges of the field of view. The Raman "image" of the uniformly Raman scattering field of view is used in the most preferred embodiment to calibrate the vignetting effect as well as the effect of local and global residual non-uniformities in the illuminating beam.

To correct for the vignetting effect as well as the effect of local and global residual nonuniformities, a uniformly Raman scattering material is illuminated with the same illumination system, and an image of the uniformly scattering material is obtained with the same imaging system as is used to illuminate and image the field of interest. The calibration image may be made of a region of a crystalline semiconductor substrate which would with perfectly uniform illumination, no vignetting effect, and uniform detector response be expected to give an image having the same number of photons in every pixel of the image detector. The actual Raman signal from each pixel, or the signal averaged over groups of pixels, is then used to calibrate images of a region of interest pixel by pixel, by methods known to those skilled in the art of image processing. In the case of inspection of implanted semiconductor materials, there may be an area of unimplanted semiconductor material on the wafer to give a field of view at least the same size as the field of view containing a feature of interest, and the image of the unimplanted region may be used as a calibration image. Otherwise, a separate unimplanted semiconductor material, or indeed any other object of material which provides a uniform Raman signal for imaging, may be used as a calibration image.

FIG. 1 shows the Raman spectra obtained from one point of a single crystal silicon and a separate region implanted with $2\times10^{15}/cm^{-2}$ arsenic ions having 150 keV energy. The sharp single crystal silicon signal at is much stronger that the broadened and shifted signal from the ion implanted amorphous region. The rotational Raman bands from air between 100 and 150 are of approximately equal strengths in each spectrum since the overall Raman signal in the ion implanted region is significantly reduced. The normalization of each data set to a similar maximum Raman intensity results in great amplification of the relative signal from the amorphous region. If a Raman window were set as a narrow band on the silicon 520 $cm^{-1}$ band and an image taken with the resulting narrow band light, the single crystal silicon regions would show much greater intensity than the amorphous regions. If on the other hand the Raman window were set as a broad band at the maximum of the amorphous signal of 480 $cm^{-1}$, the amorphous silicon would show up with much greater intensity than the single crystal silicon.

FIG. 2 shows spectra as the LCTF was tuned from 490 to 530 in 2 $cm^{-1}$ increments and normalized to the 520 $cm^{-1}$ peak. Note that the actual line shape of the 520 $cm^{-1}$ line varies little for single crystal silicon, silicon with $2.7\times10^{12}$ $cm^{-2}$ phosphorus implants, and silicon with $2\times10^{14}$ $cm^{-2}$ arsenic implant. When the spectra of FIG. 2 are plotted on the same scale in FIG. 3, however, the effect of the implants on the intensity of the single crystal silicon band at 520 $cm^{-1}$ is considerable. The higher dose of heavier arsenic almost eliminates the 520 $cm^{-1}$ signal, while the two order of magnitude lower dose of lighter phosphorous ions implant causes much less signal loss in the silicon band. The strong variation of this silicon band with implant coupled to our method of using two images to correct the relative imaging signals provides a sensitive method to quantitively determine implant dosage and its spatial uniformity.

In modem semiconductor manufacture, the ability to measure precisely the implant dose and the dose uniformity, especially for light dopants such as boron, phosphorous or beryllium which are implanted at low energy, is critical. The intensity of the silicon Raman signal is a very sensitive measure of such implant dose. Prior art measurements of such signals have not been used in metrology, because the calibration of the crystalline Silicon Raman signal is extremely difficult with the spot illumination, flying spot illumination, line focus illumination used. The inventors have realized that using flood illumination, where the entire field of view is illuminated substantially uniformly during the exposure of an image, captures an image of a silicon region and an image of the implanted region in the same image at the same time, so that the ratio of intensities of light scattered from the two regions are much more accurately measured than heretofore. This imaging approach makes use of these ratios to calibrate signals rather than an absolute measured value of the semiconductor material under study. In particular, much lighter doses of unannealed light ion implants may be accurately measured than with any other non contact, non invasive method known to the inventors.

FIG. 4 shows a Raman image and a bright field optical image of a portion of a silicon wafer with regions implanted with $2.7 \times 10^{12}/cm^{-2}$ phosphorus. The Raman image is presented in a grey scale to illustrate the extreme sensitivity and spatial features than can be see with this method. Note that the contrast between the single crystal region and the implanted region is still very high in the Raman image, and very low in the optical image. The relative variations in these signals can also be used to quantitatively obtain implant concentrations and map out concentration levels in these images.

FIG. 5 shows an image of a portion of a silicon wafer with a region implanted with $1.2 \times 10^{12}/cm^{-2}$ boron. Even in this case, with a much lighter ion and lower dose, the contrast in the Raman image is sufficient for imaging of the implant region and for measurement of the dose. The intensity of the bright field optical image in the implanted region is nearly the same as in the surrounding unimplanted region. Note also that the grey scale used for this Raman image shows a small non-isotropic distribution of the implant around the mask.

The Raman chemical imaging apparatus is especially useful in identifying defects which have small dimensions. For example, inclusions of about 1 micrometer diameter have been seen and analyzed in ion implanted silicon by TEM analysis, and shown to have a hexagonal graphitic like crystal structure. We have imaged and identified such hexagonal phase inclusions for the first time using Raman chemical imaging. While defects described here are formed by implantation, this method can also be applied equally well to detect other defects created by various semiconductor processes.

FIGS. 6 and 7 show Raman spectra of inclusions in silicon implanted with arsenic at doses of $5 \times 10^{13}/cm^2$, $2 \times 10^{14}/cm^2$, $5 \times 10^{14}/cm^2$, and $2 \times 10^{15}/cm^2$. FIGS. 6 and 7 use excitation wavelengths of 514.5 nm, and analyze the Raman scattered light having polarization parallel to the excitation wavelength. FIG. 6 has excitation polarization parallel to the (100) axis of the single crystal silicon substrate, in which there would be no Raman scattered light from the substrate alone. The peak at 520 $cm^{-1}$ for the $5 \times 10^{13}/cm^2$ implanted sample shows that the inclusion has cubic symmetry, but that the crystal axis of the inclusion is not aligned with the underlying silicon. Other inclusions for a range of higher implant dose samples have peaks around 508 $cm^{-1}$ from 505–511 $cm^{-1}$, which shows that they are from regions of the hexagonal phase of silicon.

FIG. 7 shows Raman spectra taken with excitation and analysis polarizations taken at 45 degrees with respect to the (100) axis of the underlying silicon wafer. The large peaks at 520 $cm^{-1}$ for the light implant doses show that the silicon under the inclusions is perhaps not fully amorphized.

FIG. 8 shows Raman spectra of inclusions in silicon implanted with arsenic doses of $2 \times 10^{14}/cm^2$, $5 \times 10^{14}/cm^2$, $2 \times 10^5/cm^2$ and $5 \times 10^{15}/cm^2$, taken with 488 nm excitation light, and with excitation and analysis polarization parallel to the (100) axis.

FIG. 9 shows the Raman image of a 1 micron diameter inclusion taken with Raman shifted light of 506 $cm^{-1}$ in the $5 \times 10^{15}/cm^2$ dose wafer whose spectra is shown in FIG. 8. Such inclusions have been observed with dimensions from several microns down to about 500 nm.

Obviously, many modifications and variations of the present invention are possible in light of the above teachings. It is therefore to be understood that, within the scope of the appended claims, the invention may be practiced otherwise than as specifically described.

We claim:

1. A method of inspection of an ion implanted semiconductor wafer, comprising:
    a) illuminating a surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
    b) imaging the implanted surface of the wafer using light scattered from the wafer of a wavelength which is Raman shifted in frequency from the light of wavelength $\lambda_i$;
    c) illuminating an area A of the surface of a featureless uniformly Raman Scattering material with the same illumination system as step a); then
    d) imaging the area A of the surface of the featureless uniformly Raman Scattering material using light scattered from the surface of the uniformly Raman Scattering material of a wavelength which is Raman shifted in frequency from the light of wavelength $\lambda_i$, the light imaged with the same imaging system as step (b); and
    e) correcting the image of the implanted area using the results of the imaging of the area of the surface of the uniformly Raman Scattering material.

2. A method of inspection of an ion implanted semiconductor wafer, comprising:
    a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
    b) imaging the implanted surface of the wafer using light scattered from the wafer of a wavelength which is Raman shifted in frequency from the light of wavelength $\lambda_i$; then
    c) analyzing the image for evidence of inclusions having a Raman shift peak having a full width at half maximum above 4 $cm^{-1}$ but below 30 $cm^{-1}$.

3. A method of inspection of an ion implanted semiconductor wafer, comprising:
    a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
    b) imaging the implanted surface of the wafer using light scattered from the wafer of a wavelength which is Raman shifted in frequency from the light of wavelength $\lambda_i$; then
    c) analyzing the image for evidence of inclusions having a fundamental or second order Raman shift peak having a full width at half maximum above 30 $cm^{-1}$ but below 100 $cm^{-1}$.

4. The method of claim 2, wherein the semiconductor wafer is a silicon wafer and the inclusion is an inclusion having a hexagonal phase and having a Raman shift of approximately 508 cm$^{-1}$.

5. A method of inspection of an ion implanted semiconductor wafer, comprising:
   a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$; then
   c) comparing intensity of a first image feature corresponding to an ion implanted region with intensity of a second image feature corresponding to an unimplanted single crystal semiconductor region, the first and second image features on the same image in the area A of the wafer.

6. A method of inspection of an ion implanted semiconductor wafer, comprising:
   a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$; then
   c) comparing intensity of a first image feature corresponding to an ion implanted region with intensity of a second image feature corresponding to an unimplanted single crystal semiconductor region, the first and second image features on the same image in the area A of the wafer,
   wherein the ion implanted wafer is unannealed after implantation, and wherein the ion implanted region corresponding to the first image feature has insufficient implantation dose to frilly amorphize the surface of the semiconductor wafer.

7. A method of inspection of an ion implanted semiconductor wafer comprising:
   a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$; then
   c) comparing intensity of a first image feature corresponding to an ion implanted region with intensity of a second image feature corresponding to an unimplanted single crystal semiconductor region, the first and second image features on the same image in the area A of the wafer,
   wherein the ion implanted wafer is unannealed after implantation, and wherein the ion implanted region corresponding to the first image feature has insufficient implantation dose to fully amorphize the surface of the semiconductor wafer; and
   wherein a bright field optical image of the first image feature has comparable intensity as a bright field optical image of the second image feature.

8. A method of inspection of an ion implanted semiconductor wafer comprising:
   a) illuminating an implanted surface of the ion implanted semiconductor wafer wit a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$; then
   c) comparing intensity of a first image feature corresponding to an ion implanted region with intensity of a second image feature corresponding to an unimplanted single crystal semiconductor region, the first and second image features on the same image in the area A of the wafer,
   wherein the ion implanted wafer is annealed after implantation, and wherein the ion implanted region corresponding to the first image retains at least one defect after the annealing.

9. A method of inspection of an ion implanted semiconductor wafer comprising:
   a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$; then
   c) comparing intensity of a first image feature corresponding to an ion implanted region with intensity of a second image feature corresponding to an unimplanted single crystal semiconductor region, the first and second image features on the same image in the area A of the wafer,
   wherein the ion implanted region corresponding to the first image contains hexagonal phase defects.

10. A method of inspection of an ion implanted semiconductor wafer comprising:
   a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then
   b) imaging the implanted surface of the wafer using light scattered from the wafer of a wavelength which is Raman shifted in frequency from the light of wavelength $\lambda_i$, wherein the imaging is in a first spatial dimension and one Raman shifted wavelength dimension, wherein a second spatial dimension is kept constant, then c) imaging a number of further images, wherein each image is imaged using light from a different value of the second spatial dimension.

11. A method of inspection of an ion implanted semiconductor wafer, comprising:

a) illuminating an implanted surface of the ion implanted semiconductor wafer with a flood illumination of monochromatic light of wavelength $\lambda_i$, the flood illumination illuminating at least an area A of the wafer, the implanted surface having Raman active features induced by the ion implantation; then b) imaging the implanted surface of the wafer using light scattered from the wafer of a wavelength which is Raman shifted in frequency from the light of wavelength $\lambda_i$; then c) imaging a further plurality of images, each of the imaging using a different illuminating monochromatic wavelength $\lambda_p$, and wherein the depth distribution of the features producing the Raman shifted light for each illuminating wavelength $\lambda_p$ is calculated from the plurality of images.

\* \* \* \* \*